(12) United States Patent
Lazic

(10) Patent No.: US 8,273,096 B2
(45) Date of Patent: Sep. 25, 2012

(54) ANEURYSM CLIP

(75) Inventor: Daniel Lazic, Tuttlingen (DE)

(73) Assignee: Peter Lazic GmbH, Tuttlingen (DE)

( * ) Notice: Subject to any disclaimer, the term of this patent is extended or adjusted under 35 U.S.C. 154(b) by 245 days.

(21) Appl. No.: 12/782,913

(22) Filed: May 19, 2010

(65) Prior Publication Data

US 2010/0298849 A1    Nov. 25, 2010

(30) Foreign Application Priority Data

May 20, 2009    (DE) .................. 10 2009 003 273

(51) Int. Cl.
*A61B 17/08* (2006.01)
(52) U.S. Cl. .................. 606/158; 24/510
(58) Field of Classification Search .......... 606/142, 606/151, 157, 158; 24/456, 500, 508–510
See application file for complete search history.

(56) References Cited

U.S. PATENT DOCUMENTS

| | | | | |
|---|---|---|---|---|
| 1,589,076 A | * | 6/1926 | Haskins | .......................... 24/483 |
| 4,932,955 A | * | 6/1990 | Merz et al. | ..................... 606/158 |
| 5,197,879 A | | 3/1993 | Fowler, III et al. | |
| 2002/0111643 A1 | * | 8/2002 | Herrmann et al. | ............. 606/158 |

FOREIGN PATENT DOCUMENTS

DE    10 2004 016 859 A1    10/2005

* cited by examiner

*Primary Examiner* — Tuan V Nguyen
(74) *Attorney, Agent, or Firm* — Walter A. Hackler

(57) ABSTRACT

An aneurysm clip with two rotatably connected scissors-shaped clip parts, each part having one clamping arm and one operating arm. The two clip parts are guided in such a fashion that they can be rotated in a working rotation range between a closed and an open end position. The two clip parts are connected to each other by a push-fit rotary lock, with the two clip parts axially inserted into one another in an open assembly rotation position outside of the working rotation range, and are axially locked to one another by subsequent rotation into the working rotation range.

7 Claims, 3 Drawing Sheets

ANEURYSM CLIP

CROSS REFERENCE TO RELATED APPLICATIONS

This application claims priority under 35 U.S.C. §119(a) to German Patent Application No. 10 2009 003 273.8, filed May 20, 2009, the entire contents of which are hereby incorporated by reference.

TECHNICAL FIELD

The invention relates to an aneurysm clip with two rotatably connected scissors-shaped clip parts, each having one clamping arm and one operating arm, wherein the two clip parts are guided in such a fashion that they can be rotated in a working rotation range between a closed and an open end position.

BACKGROUND

An aneurysm clip of this type is disclosed e.g. in DE 10 2004 016 859 A1.

The aneurysm clip disclosed in DE 10 2004 016 859 A1 comprises two clip parts, one of which, the first clip part, being inserted into a rotary receptacle of the other, second clip part and secured therein by a small guiding plate. This small guiding plate is welded to the second clip part after fitting together the two clip parts, thereby preventing detachment of the two clip parts in a direction opposite to the fitting direction. However, welding of the small guiding plate requires complex assembly, in which the welded plate is subsequently machined in order to prevent formation of flashes.

In contrast thereto, it is the object of the present invention to further develop an aneurysm clip of the above-mentioned type in such a fashion that subsequent machining is not required, thereby improving the surface quality.

SUMMARY

This object is achieved in accordance with the invention in that the two clip parts are connected to each other via a push-fit rotary lock, wherein the two clip parts are axially inserted into one another in an open assembly rotation position located, in particular, outside of the working rotation range, and are axially locked to each other by subsequent rotation in the working rotation range.

The inventive push-fit rotary lock permits the two clip parts to be inserted into one another and be rotatably guided without additional components.

In one particularly preferred embodiment of the invention, each of the two clip parts has an axially open receptacle, the bottom of which has two oppositely disposed pivot guide sections on the outer periphery and respectively interposed assembly recesses, the two clip parts each having two pivot bearing sections disposed opposite to each other with respect to the receptacle for the pivot guide sections of the respective other clip part, wherein the pivot bearing sections of the second clip part are formed as guiding grooves and in the assembly rotation position, the two clip parts are axially fitted into one another with their two assembly recesses between the two pivot bearing sections of the respective other clip part and can be transferred by subsequent rotation into the working rotation range in which the pivot guide sections of the first clip part engage in the guiding grooves of the second clip part.

A closing spring is preferably disposed in a through-hole which is formed by bores of the two clip parts, which bores are centered with respect to the axis of rotation, the closing spring pretensioning the two clip parts into their closed end position.

The pivot guide sections of one clip part and the assembly recesses of the other clip part are preferably disposed with respect to angular position and angular length such that the two clip parts can be axially fitted into one another only in one single assembly rotation position.

With particular preference, each pivot bearing section of the second clip part is overlapped on the side facing away from the bottom by a protrusion and is thereby formed as a guiding groove. For reasons of manufacturing technology, the second clip part is advantageously formed identically to the first clip part except for the protrusions.

Further advantages of the invention can be extracted from the description, the claims and the drawing. The features mentioned above and below may be used individually or collectively in arbitrary combination. The embodiments shown and described are not to be understood as exhaustive enumeration but have exemplary character for describing the invention.

DETAILED DESCRIPTION

Figures 1A, 1B:
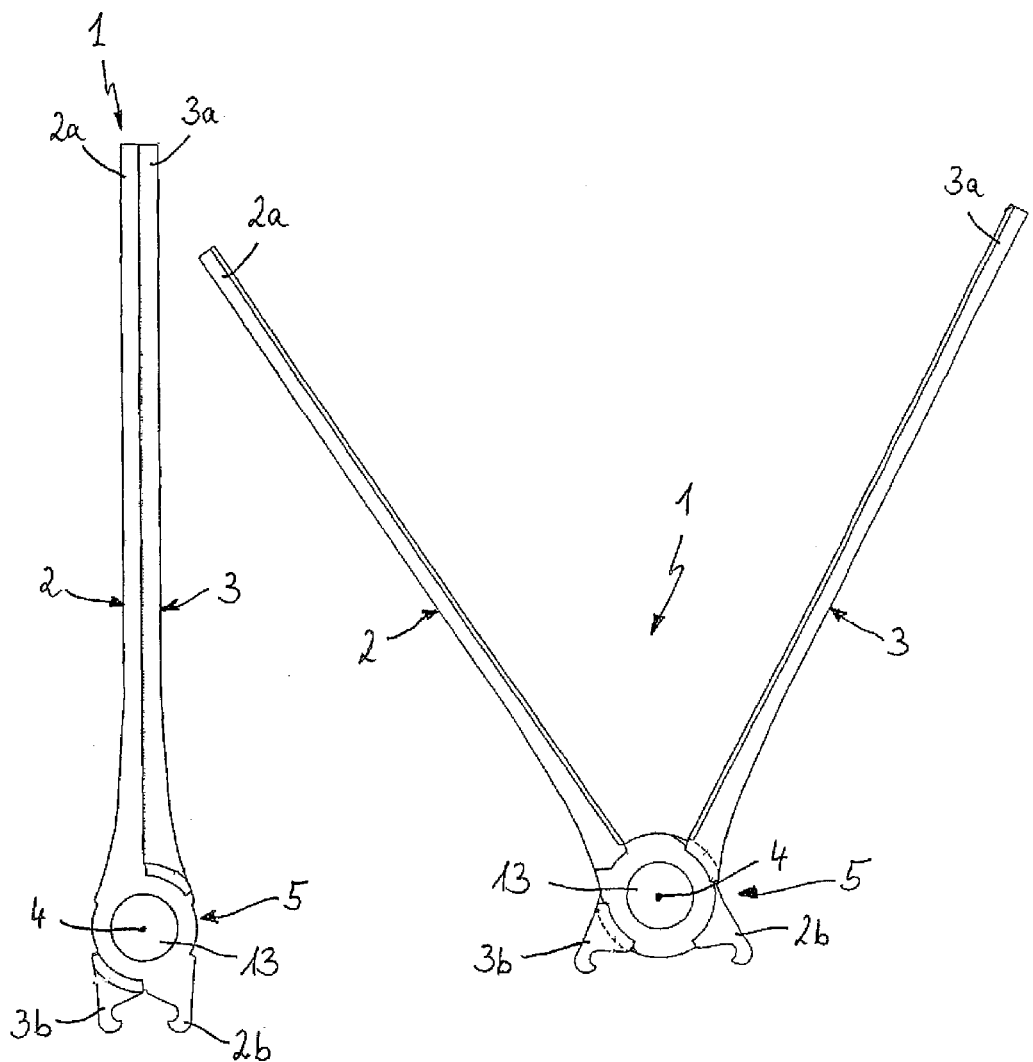
FIGS. 1a, 1b show the inventive aneurysm clip in the closed state (FIG. 1a) and in an assembly rotation position with maximum width opening (FIG. 1b), wherein a closing spring is not shown.

The aneurysm clip 1 shown in FIGS. 1a, 1b comprises two scissors-shaped clip parts 2, 3 which are connected to each other and can be rotated about an axis of rotation 4. The two clip parts 2, 3 each have a clamping arm 2a, 3a and an operating arm (operating branch) 2b, 3b, which are disposed opposite to each other with respect to the axis of rotation 4. The operating arms 2b, 3b can be forced apart against the force of a closing spring (not shown) by means of applying forceps which engage between the two operating arms 2b, 3b, thereby opening the clamping arms 2a, 3a.

The two clip parts 2, 3 are guided in such a fashion that they can be rotated in a working rotation range between the closed end position shown in FIG. 1a, in which the two clamping arms 2a, 3a abut each other, and an open end position. As is described in more detail below, the two clip parts 2, 3 are connected to each other by a push-fit rotary fastener 5, wherein the two clip parts 2, 3 are axially fitted into one another in a maximally opened assembly rotation position (FIG. 1b) located outside of the working rotation range, and are axially locked to each other by subsequent rotation into the working rotation range.

Figure 2A:
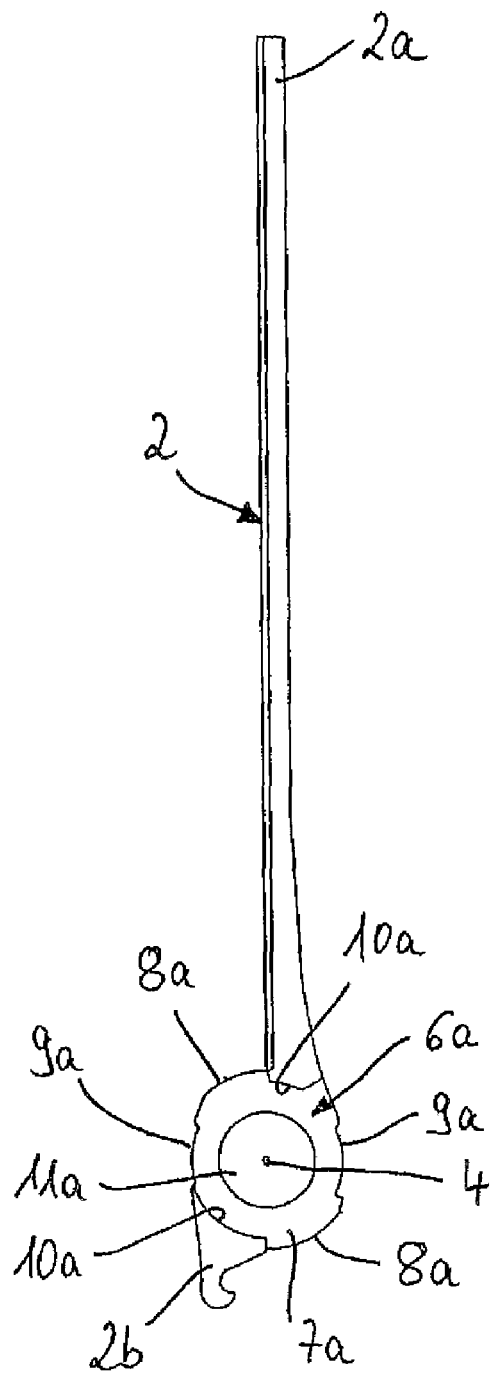
FIGS. 2a, 2b show a first clip part of the aneurysm clip shown in FIG. 1 in top view (FIG. 2a) and in side view (FIG. 2b)
Figure 2B:
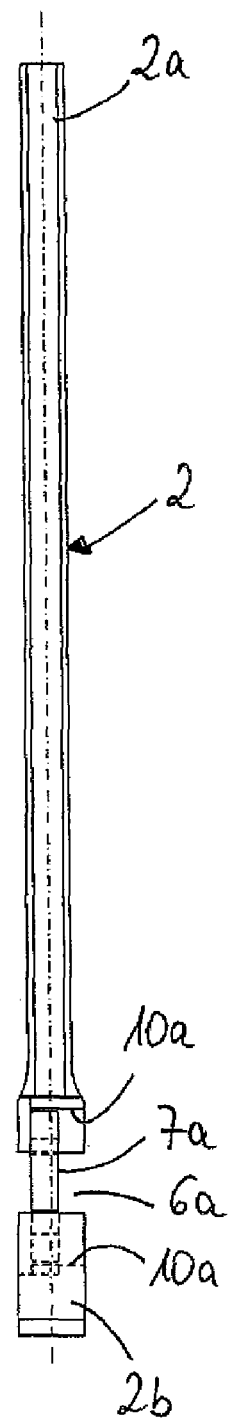

As is shown in FIGS. 2a, 2b, the first clip part 2 has an axially open receptacle 6a, the bottom or base plate 7a of which has two oppositely disposed pivot guide sections 8a on the outer periphery and respectively interposed radially inwardly projecting assembly recesses 9a. The transition area between the base plate 7a and the clamping arm 2a or operating arm 2b is provided with two pivot bearing sections 10a which are disposed opposite to each other with respect to the receptacle 6a, face the axis of rotation 4, and are each formed by a step on the clamping arm 2a and on the operating arm 2b.

The bottom plate 7a has a bore 11a which is centered with respect to the axis of rotation 4.

Figures 3A, 3B:
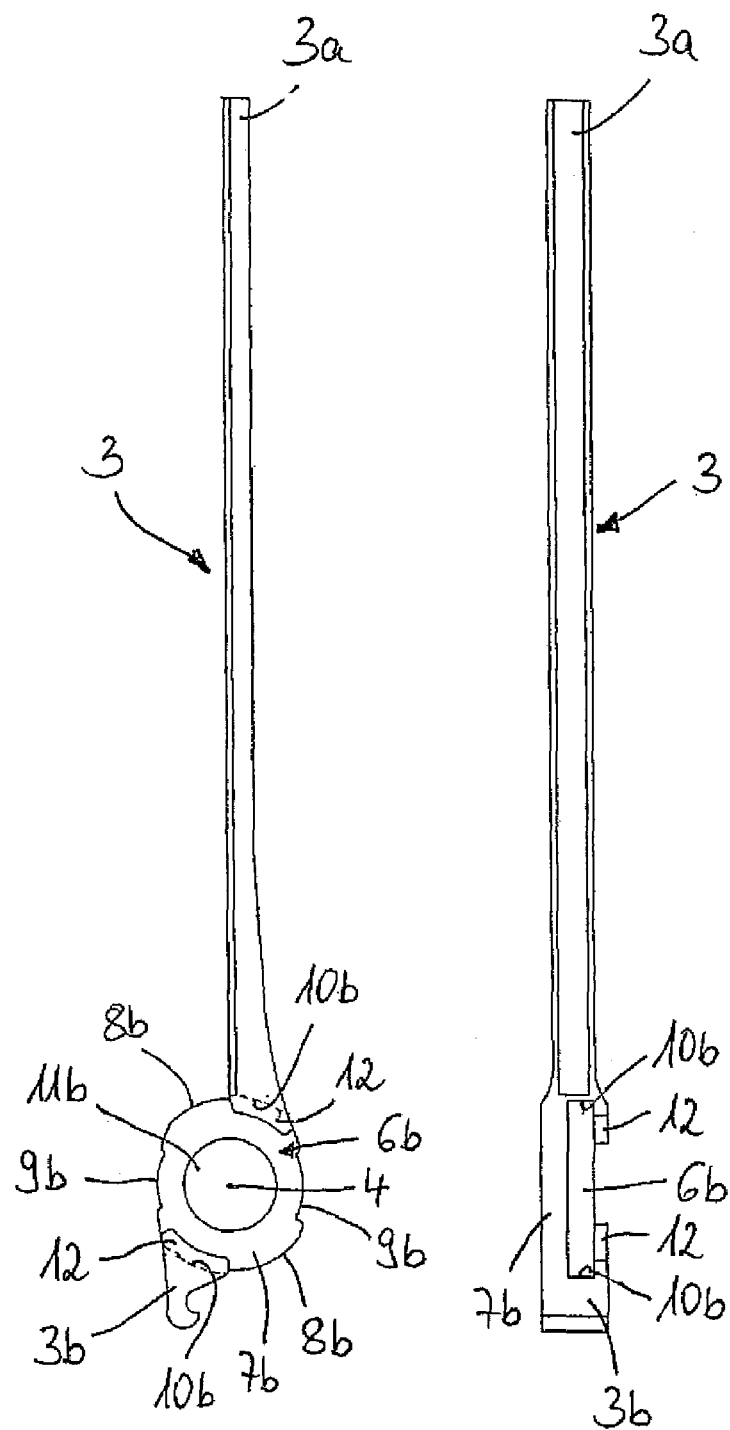
FIGS. 3a, 3b show a second clip part of the aneurysm clip shown in FIG. 1 in top view (FIG. 3a) and in side view (FIG. 3b).

As is shown in FIGS. 3a, 3b, the other, second clip part 3 has an axially open receptacle 6b, the bottom or base plate 7b of which has two oppositely disposed pivot guide sections 8b on the outer periphery and respectively interposed assembly recesses 9b. Two pivot bearing sections 10b which are disposed opposite to each other with respect to the receptacle 6b are provided at the transition area between the base plate 7b and the clamping arm 3a or operating arm 3b, face the axis of rotation 4, and are each formed by a step on the clamping arm 3a and on the operating arm 3b. The base plate 7b has a bore 11b which is centered with respect to the axis of rotation 4. Each pivot bearing section 10b is overlapped by a protrusion 12 on the side opposite to the base plate 7b and thereby formed as a guiding groove. The second clip part 3 is identical to the first clip part 2 except for its two protrusions 12.

The two assembly recesses 9a, 9b of the clip parts 2, 3 are respectively oriented between the two pivot bearing sections 8b, 8a of the respective other clip part for connecting the two clip parts 2, 3 to form an aneurysm clip 1, and are axially fitted into one another in the assembly rotation position shown in FIG. 1b until their bottom plates 7a, 7b abut each other. The two clip parts 2, 3 are subsequently transferred into the working rotation range through rotation, in which the pivot guide sections 8a of the first clip part 2 engage in the guiding grooves 10b of the second clip part 3 and are pivoted therein, and the pivot guide sections 8b of the second clip part 3 are also pivoted on the pivot bearing sections 10a of the first clip part 2. Due to the engagement of the pivot guide sections 8a in the guiding grooves 10b, the two clip parts 2, 3 are axially connected to each other in the working rotation range and are locked in a direction opposite to the fitting direction.

The pivot guide sections 8a, 8b and the assembly recesses 9b, 9a of the two clip parts 2, 3 are arranged with respect to angular position and angular length such that the two clip parts 2, 3 can be axially fitted into one another only in the illustrated assembly rotation position.

The central bores 11a, 11b of the connected clip parts 2, 3 form a through-hole 13 into which a leg spring (not shown) is inserted, the two leg ends of which are respectively welded to the clip parts 2, 3. As a result, the two clip parts 2, 3 are pretensioned into their closed end position and also secured in the direction opposite to the fitting direction.

What is claimed is:

1. Aneurysm clip comprising: two rotatably connected scissors-shaped clip parts, each having one clamping arm and one operating arm, the two clip parts being rotatable in a working rotation range between a closed and an open end position each of the two clip parts having a bottom plate, an axially open receptacle with a two oppositely disposed pivot guide sections on the outer periphery and respectively interposed assembly recesses, the two clip parts each comprises two pivot bearing sections, disposed opposite to each other with respect to the open receptacle, for the pivot guide sections of the respective other clip parts, wherein the pivot bearing sections of the second clip pat are frothed as guiding grooves, and in the assembly rotation position, the two clip parts are axially fitted into one another with two assembly recesses between the two pivot bearing sections of the respective other clip part and are transferred, by a subsequent rotary motion, into the working rotation range in which the pivot guide sections of the first clip part engage in the guiding grooves of the second clip part; a closing spring is disposed in a through-hole which is formed by bores of the two clip parts, which the bores are being centered with respect to an axis of rotation , the two clip parts being pretensioned into the closed position by the closing spring; and a push-fit rotary lock connecting the two clip parts to each other, the two clip parts being axially inserted into one another in an open assembly rotation position, the position being disposed outside of the working rotation range, the clip parts are axially locked to one another by subsequent rotation into the working rotation range.

2. Aneurysm clip according to claim 1, wherein the pivot guide sections of one clip part and the assembly recesses of the other clip part are disposed with respect to angular position and angular length such that the two clip parts can be axially fitted into one another only in one single assembly rotation position.

3. Aneurysm clip according to claim 1, wherein each pivot bearing section of the second clip part is overlapped by one protrusion on the side facing away from the bottom plate and thereby formed as a guiding groove.

4. Aneurysm clip according to claim 3, wherein the second clip part is identical to the other clip part except for its protrusions.

5. Aneurysm clip according to claim 1, wherein the pivot bearing sections are formed by steps on the clamping arm and on the operating arm.

6. Aneurysm clip according to claim 1, wherein the pivot bearing sections of the two clip parts face the axis of rotation.

7. Aneurysm clip according to claim 1,
wherein the pivot guide sections of one clip part and the assembly recesses of the other clip part are disposed with respect to angular position and angular length such that the two clip parts can be axially fitted into one another only in one single assembly rotation position, wherein each pivot bearing section of the second clip part is overlapped by one protrusion on the side facing away from the bottom plate and thereby formed as a guiding groove, wherein the second clip part is identical to the first clip part except for its protrusions, wherein the pivot bearing sections are formed by steps on the clamping arm and on the operating arm, and wherein the pivot bearing sections of the two clip parts face the axis of rotation.

\* \* \* \* \*